(12) United States Patent
Dosier et al.

(10) Patent No.: US 12,195,392 B2
(45) Date of Patent: Jan. 14, 2025

(54) COMPOSITIONS AND METHODS FOR DUST CONTROL

(71) Applicant: Biomason Inc., Research Triangle Park, NC (US)

(72) Inventors: Ginger K. Dosier, Raleigh, NC (US); Victoria M. Durham, San Diego, CA (US); Thomas A. Hill, Dacula, GA (US); J. Michael Dosier, Raleigh, NC (US); Steven W. McAllister, Durham, NC (US)

(73) Assignee: Biomason Inc., Durham, NC (US)

( * ) Notice: Subject to any disclaimer, the term of this patent is extended or adjusted under 35 U.S.C. 154(b) by 0 days.

(21) Appl. No.: 17/570,312

(22) Filed: Jan. 6, 2022

(65) Prior Publication Data

US 2022/0126317 A1 Apr. 28, 2022

Related U.S. Application Data

(63) Continuation of application No. 16/781,622, filed on Feb. 4, 2020, now abandoned, which is a continuation of application No. 15/066,692, filed on Mar. 10, 2016, now abandoned.

(60) Provisional application No. 62/200,288, filed on Aug. 3, 2015, provisional application No. 62/188,556, filed on Jul. 3, 2015, provisional application No. 62/130,854, filed on Mar. 10, 2015.

(51) Int. Cl.
| | | |
|---|---|---|
| *C04B 12/00* | (2006.01) | |
| *B05D 1/02* | (2006.01) | |
| *C04B 28/10* | (2006.01) | |
| *C04B 103/00* | (2006.01) | |
| *C04B 111/00* | (2006.01) | |
| *C04B 111/60* | (2006.01) | |
| *C12N 11/02* | (2006.01) | |
| *C12N 11/14* | (2006.01) | |

(52) U.S. Cl.
CPC ............ *C04B 12/00* (2013.01); *B05D 1/02* (2013.01); *C04B 28/10* (2013.01); *C12N 11/02* (2013.01); *C12N 11/14* (2013.01); *C12Y 305/01005* (2013.01); *C04B 2103/0001* (2013.01); *C04B 2103/0075* (2013.01); *C04B 2111/00146* (2013.01); *C04B 2111/60* (2013.01); *Y02W 30/91* (2015.05)

(58) Field of Classification Search
CPC . C04B 12/00; C04B 28/10; C04B 2103/0001; C04B 2103/0075; C04B 2111/60; C04B 24/126; C04B 2111/0075; B05D 1/02; C12N 11/02; C12N 11/14; C12Y 305/01005; Y02W 30/91; A61L 24/0036
See application file for complete search history.

(56) References Cited

U.S. PATENT DOCUMENTS

| | | |
|---|---|---|
| 3,667,976 A | 6/1972 | Tanner et al. |
| 3,829,553 A | 8/1974 | Lynn |
| 4,204,876 A | 5/1980 | Bowden |
| 4,617,326 A | 10/1986 | Bjornberg et al. |
| 4,946,505 A | 8/1990 | Jungk |
| 5,143,155 A | 9/1992 | Ferris et al. |
| 5,199,986 A | 4/1993 | Krockert et al. |
| 5,558,708 A | 9/1996 | Johansen, Jr. et al. |
| 5,846,315 A | 12/1998 | Johansen, Jr. et al. |
| 5,891,205 A | 4/1999 | Picardi et al. |
| 6,348,147 B1 | 2/2002 | Long |
| 7,025,824 B2 | 4/2006 | Axen et al. |
| 7,101,430 B1 | 9/2006 | Pike et al. |
| 8,182,604 B2 | 5/2012 | Kucharski et al. |
| 8,420,362 B2 | 4/2013 | Crawford et al. |
| 8,470,275 B2 | 6/2013 | Constantz et al. |
| 8,518,177 B2 | 8/2013 | Chattopadhyay et al. |
| 8,728,365 B2 | 5/2014 | Dosier |

(Continued)

FOREIGN PATENT DOCUMENTS

| | | |
|---|---|---|
| CA | 2591097 A1 | 6/2006 |
| CN | 1101626 A | 4/1995 |

(Continued)

OTHER PUBLICATIONS

Wang et al., Application of hydrogel encapsulated carbonate precipitating bacteria for approaching a realistic self-healing in concrete. Construction and Building Materials, 2014, vol. 68: 110-119. (Year: 2014).*

(Continued)

*Primary Examiner* — Ganapathirama Raghu
(74) *Attorney, Agent, or Firm* — Tyler Thorp; Newport IP, LLC

(57) ABSTRACT

Compositions and methods for producing materials for construction and for dust control utilizing enzyme producing cells, an amount of a nitrogen source such as urea, and an amount of calcium such as calcium chloride. Calcium contributes to the formation of calcium carbonate which creates a solid structure, layer or shield. One or more compositions containing components of the invention can be sprayed or otherwise applied to surfaces for erosion control, foundation support, prevention of sink hole formation, prevention of dust formation, or other applications. Ammonia, water and other by-products of the process can be recycled and re-utilized for the same or other purposes including, for example, as fertilizers and energy sources, or independently fermented from selectively cultivated microorganisms.

20 Claims, No Drawings

(56) References Cited

U.S. PATENT DOCUMENTS

| | | |
|---|---|---|
| 8,911,549 B2 | 12/2014 | Jonkers |
| 8,912,244 B2 | 12/2014 | Vitomir et al. |
| 8,932,400 B2 | 1/2015 | Chen et al. |
| 8,951,786 B1 | 2/2015 | Dosier |
| 9,074,134 B2 | 7/2015 | Bang et al. |
| 9,199,880 B2 | 12/2015 | Dosier |
| 9,428,418 B2 | 8/2016 | Dosier |
| 9,796,626 B2 | 10/2017 | Dosier |
| 10,125,303 B2 | 11/2018 | Wilson et al. |
| 10,450,695 B2 | 10/2019 | Dosier et al. |
| 10,626,547 B2 | 4/2020 | Dosier et al. |
| 10,717,674 B2 | 7/2020 | Hill et al. |
| 11,008,591 B2 | 5/2021 | Dosier et al. |
| 11,472,738 B2 | 10/2022 | Hill et al. |
| 11,795,108 B2 | 10/2023 | Smith |
| 2005/0029187 A1 | 2/2005 | Koga et al. |
| 2005/0103204 A1 | 5/2005 | Halliday et al. |
| 2005/0103234 A1 | 5/2005 | McNulty, Jr. |
| 2007/0216058 A1 | 9/2007 | Carreras-Maldonado et al. |
| 2008/0245272 A1 | 10/2008 | Kucharski et al. |
| 2010/0086367 A1 | 4/2010 | Darson-Baulleur et al. |
| 2010/0210745 A1 | 8/2010 | McDaniel et al. |
| 2011/0011303 A1 | 1/2011 | Jonkers |
| 2011/0027850 A1 | 2/2011 | Crawford et al. |
| 2011/0067600 A1 | 3/2011 | Constantz et al. |
| 2012/0199046 A1 | 8/2012 | Jonkers |
| 2013/0112114 A1 | 5/2013 | Jonkers |
| 2013/0196419 A1 | 8/2013 | Chavez Crooker et al. |
| 2014/0248681 A1 | 9/2014 | Soens et al. |
| 2014/0369749 A1 | 12/2014 | Friedman et al. |
| 2015/0264898 A1 | 9/2015 | Ortego et al. |
| 2015/0322604 A1 | 11/2015 | Brunner et al. |
| 2016/0010434 A1 | 1/2016 | Portman et al. |
| 2016/0090328 A1 | 3/2016 | Wiktor et al. |
| 2016/0130489 A1 | 5/2016 | Gilmour |
| 2016/0174530 A1 | 6/2016 | Barber |
| 2016/0264463 A1 | 9/2016 | Dosier et al. |
| 2017/0015832 A1 | 1/2017 | Berlin et al. |
| 2017/0190620 A1 | 7/2017 | Jonkers et al. |
| 2018/0118623 A1 | 5/2018 | Smith et al. |
| 2018/0244585 A1 | 8/2018 | Rahbar et al. |
| 2019/0106717 A1 | 4/2019 | Dosier et al. |
| 2019/0210924 A1 | 7/2019 | Royne et al. |
| 2020/0171533 A1 | 6/2020 | Dosier et al. |
| 2020/0262711 A1 | 8/2020 | Dosier et al. |
| 2020/0331804 A1 | 10/2020 | Hill et al. |
| 2020/0346976 A1 | 11/2020 | Hill et al. |
| 2021/0189238 A1 | 6/2021 | Kavazanjian et al. |
| 2021/0395146 A1 | 12/2021 | Dosier et al. |

FOREIGN PATENT DOCUMENTS

| | | |
|---|---|---|
| CN | 1125472 A | 6/1996 |
| CN | 1285401 A | 2/2001 |
| CN | 1778934 A | 5/2006 |
| CN | 1807358 A | 7/2006 |
| CN | 101270369 A | 9/2008 |
| CN | 101054568 B | 5/2010 |
| CN | 102121033 A | 7/2011 |
| CN | 102587875 A | 7/2012 |
| CN | 103173376 A | 6/2013 |
| CN | 103173376 B | 10/2014 |
| CN | 104071890 A | 10/2014 |
| CN | 105080932 A | 11/2015 |
| CN | 105418013 A | 3/2016 |
| CN | 105837075 A | 8/2016 |
| CN | 105884308 A | 8/2016 |
| CN | 105924053 A | 9/2016 |
| CN | 105925512 A | 9/2016 |
| CN | 108956667 A | 12/2018 |
| EP | 0388304 A1 | 9/1990 |
| EP | 0631998 A1 | 1/1995 |
| EP | 1838642 A1 | 10/2007 |
| EP | 1893546 A1 | 3/2008 |
| EP | 2082999 A1 | 7/2009 |
| EP | 2247551 A1 | 11/2010 |
| EP | 2297062 A1 | 3/2011 |
| EP | 2429970 A1 | 3/2012 |
| EP | 2462232 A2 | 6/2012 |
| EP | 2940122 A1 | 11/2015 |
| JP | S63227330 A | 9/1988 |
| JP | H05253908 A | 10/1993 |
| JP | 2006144285 A | 6/2006 |
| JP | 2007284974 A | 11/2007 |
| JP | 2008524096 A | 7/2008 |
| JP | 2009270302 A | 11/2009 |
| JP | 2011509915 A | 3/2011 |
| JP | 2012019751 A | 2/2012 |
| JP | 2013523590 A | 6/2013 |
| JP | 5253908 B2 | 7/2013 |
| JP | 5284646 B2 | 9/2013 |
| JP | 2014510689 A | 5/2014 |
| WO | WO-0248069 A1 | 6/2002 |
| WO | WO-03055450 A1 | 7/2003 |
| WO | WO-2006066326 A1 | 6/2006 |
| WO | WO-2007044439 A2 | 4/2007 |
| WO | WO-2007070706 A2 | 6/2007 |
| WO | WO-2008009771 A1 | 1/2008 |
| WO | WO-2008120979 A1 | 10/2008 |
| WO | WO-2009009838 A1 | 1/2009 |
| WO | WO-2009093898 A1 | 7/2009 |
| WO | WO-2010130712 A1 | 11/2010 |
| WO | WO-2011126361 A1 | 10/2011 |
| WO | WO-2011137106 A1 | 11/2011 |
| WO | WO-2012113765 A1 | 8/2012 |
| WO | WO-2013120847 A1 | 8/2013 |
| WO | WO-2014185781 A1 | 11/2014 |
| WO | WO-2015042031 A1 | 3/2015 |
| WO | WO-2015155769 A1 | 10/2015 |
| WO | WO-2016010434 A1 | 1/2016 |
| WO | WO-2016144786 A1 | 9/2016 |
| WO | WO-2016145190 A1 | 9/2016 |
| WO | WO-2017139750 A1 | 8/2017 |
| WO | WO-2017189106 A1 | 11/2017 |
| WO | WO-2017220768 A1 | 12/2017 |
| WO | WO-2018064320 A1 | 4/2018 |
| WO | WO-2018081542 A1 | 5/2018 |
| WO | WO-2018200684 A1 | 11/2018 |
| WO | WO-2019071172 A1 | 4/2019 |
| WO | WO-2019071175 A1 | 4/2019 |
| WO | WO-2020168342 A1 | 8/2020 |
| WO | WO-2020180914 A1 | 9/2020 |
| WO | WO-2020198295 A1 | 10/2020 |
| WO | WO-2022010915 A1 | 1/2022 |

OTHER PUBLICATIONS

Co-pending U.S. Appl. No. 17/822,067, inventors Hill; Thomas A. et al., filed Aug. 24, 2022.

JP2021-130497 Search Report dated Aug. 29, 2022 (w/ English translation).

Ivanov et al. Sustainable and Safe Construction Biomaterials: Biocements and Biogrouts. Frontiers in Biomaterials, vol. 6, pp. 177-193 (2019).

Achal, Varenyam, et al., "Biogenic Treatment Improves the Durability and Remediates the Cracks of Concrete Structures", Construction and Building Materials, 2013, vol. 48, pp. 1-5.

Application of Bacteria as Self-Healing Agent for the Development of Sustainable Concrete, H.M. Jonkers et al., Ecological Engineering 36:230-235, 2010.

Australian Examination Report for 2016/228974 dated May 25, 2018.

Australian Office action for AU Application No. 2018226428 dated Feb. 21, 2020.

Australian Search Report for 2016/228974 dated Feb. 23, 2018.

Bang et al., "Calcite precipitation induced by polyurethane immobilized Bacillus pasteurii", Enzyme and Microbial Technology, 2001, vol. 28, pp. 404-409.

Beck et al. On the use of eggshell lime and tuffeau powder to formulate an appropriate mortar for restoration purposes. From Smith et al., eds. Limestone in the Built Environment: Present-Day

(56) References Cited

OTHER PUBLICATIONS

Challenges for the Preservation of the Past. Geological Society, London, Special Publications, 331, 137-145 (Jan. 1, 2010).
BioZEment (completed). Web Page. UiO Department of Physics. Published Nov. 3, 2014. Last modified Nov. 27, 2017. Retrieved Oct. 22, 2021 at URL: https://www.mn.uio.no/fysikk/english/research/projects/biozement/. 5 pages.
BR 112017017145-7 Office Action and Search Report dated Jan. 21, 2020 (w/ English summary).
Bundur et al., Biomineralized cement-based materials: impact of inoculating vegetative bacterial cells on hydration and strength. Cement and Concrete Res., 2015, vol. 67: 237-245. Available online Oct. 27, 2014.
Castro-Alonso et al., Microbially Induced Calcium Carbonate Precipitation (MICP) and Its Potential in Bioconcrete: Microbiological and Molecular concepts. Frontiers in Materials, 2019, vol. 6, Article 126: 1-15.
Chekroun et al. Precipitation and Growth Morphology of Calcium Carbonate Induced by Myxococcus Xanthus: Implications for Recognition of Bacterial Carbonates. Journal of Sedimentary Research 74 (6): 868-876 (2004).
Cho et al, "Effect of Surfactants on CO2 Biomineralization with *Sporosarcina pasteurii* and *Bacillus megaterium*", Water Air Soil Pollut., 2015, vol. 226:2245, pp. 1-12.
Choi, Sun-Gyu, et al., "Biocementation for Sand Using an Eggshell as Calcium Source", Journal of Geotech, Journal of Geotechnical and Geoenvironmental Engineering, Technical Note, 2016, pp. 1-4.
Choi, Sun-Gyu, et al., "Properties of Biocemented, Fiber Reinforced Sand", Construction and Building Materials, 2016, vol. 120, pp. 623-629.
Chu, Jian, et al., "Proof of Concept: Biocement for Road Repair", Final Report, Mar. 2015, Iowa State University, Midwest Transportation Center, 15 Pages.
Chu, Jian, "Solutions to Sustainability in Construction: Some Examples", Procedia Engineering, 2016, vol. 145, pp. 1127-1134.
Cichoż-Lach et al. Current pathogenetic aspects of hepatic encephalopathy and noncirrhotic hyperammonemic encephalopathy. World J Gastroenterol. Jan. 7, 2013;19(1):26-34.
CN201680013219.2 Office Action dated Jan. 31, 2021 (w/ English summary).
CN201680013219.2 Office Action dated Jul. 27, 2020 (w/ English summary).
CN201680013219.2 Office Action with Search Report dated Aug. 21, 2019 (w/ English summary).
Co-pending U.S. Appl. No. 16/933,171, inventors Hill; Thomas A. et al., filed Jul. 20, 2020.
Cree et al. Sustainable Bio-Inspired Limestone Eggshell Powder for Potential Industrialized Applications. ACS Sustainable Chem Eng 3, 941-949 (Apr. 9, 2015).
Cunningham, A.B., et al., "Reducing the Risk of Well Bore Leakage of CO2 Using Engineered Biomineralization Barriers", Energy Procedia, 2011, vol. 4, pp. 5178-5185.
Cuzman et al., Bacterial "Masons" at work with wastes for producing eco-cement. Int. J. Environ. Sci. Develop., 2015, vol. 6(10): 767-774.
Day, Jeremy L. et al, Microbiologically Induced Sealant for Concrete Crack Remediation, https://www.ce.washingtonedu/em2003/proceedings/papers/352.pdf (2003).
De Muynck, Willem et al, Microbial Carbonate Precipitation in Construction Materials: A Review, Ecological Engineering, 2010, pp. 118-136, vol. 36, Elsevier.
Dejong, Jason T. et al, Bio-mediated Soil Improvement; Ecological Engineering, 2009, pp. 197-210, vol. 36, Elsevier.
Dejong, Jason T. et al, Microbially Induced Cementation to Control Sand Response to Undrained Shear, Journal of Geotechnical and Geoenvironmental Engineering, Nov. 2006, pp. 1381-1392, ASCE.
EP16762507.8 Extended European Search Report dated Mar. 14, 2019.
EP16762507.8 Partial Supplementary European Search Report dated Oct. 9, 2018.
Examination Report for CA Application No. 3,003,894 dated Mar. 29, 2019.
Examination Report for EP Application No. 16 762 507.8 dated Sep. 28, 2018.
Examination Report for IN Application No. 201717028629 dated Mar. 29, 2019.
Examination Report for JP Application No. 2017-566616 dated Feb. 8, 2021 (with translation).
Examination Report for JP Application No. 2017-566616 dated May 20, 2019 (with English translation).
Examination Report for JP Application No. 2018-242426 dated Aug. 24, 2020 (with English translation).
F. D. Meyer et al, "Microbiologically-Induced Soil Stabilization: Application of *Sporosarcina pasteurii* for Fugitive Dust Control", Geo-Frontiers 2011, Reston, VA, (Mar. 11, 2011), doi:10.1061/41165(397)409, ISBN 978-0-7844-1165-0, pp. 4002-4011, XP055562331.
Ferris, F.G. et al, Bacteriogenic Mineral Plugging, Petroleum Society of CIM and CANMET, Paper No. 11, presented at the CIM/CANMET Fourth Petroleum Conference held in Regina, Sask., pp. 11-1 to 11-12, Oct. 7-9, 1991.
Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.
Fujita, Yoshiko, et al., Evaluating the Potential of Native Ureolytic Microbes to Remediate a 90Sr Contaminated Environment, Environmental Science & Technology, 2010, vol. 44, No. 19, pp. 7652-7658.
Fukue et al, Grain growth of carbonates using ureolytic microbes, Japanese Geotechnical Journal, (2011), vol. 6, No. 3, pp. 455-464, with English translation of abstract.
Ghosh, P., et al., "Use of Microorganism to Improve the Strength of Cement Mortar", Cement and Concrete Research, 2005, vol. 35, pp. 1980-1983.
Gleb B. Sukhorukov et al., "Porous calcium carbonate microparticles as templates for encapsulation of bioactive compounds" J. Mater. Chem. 14:2073-2081, 2004.
Gollapudi, U.K. et al, A New Method for Controlling Leaching Through Permeable Channels, Chemosphere, 1995, pp. 695-705, vol. 30, No. 4, Elsevier Science Ltd., Great Britain.
Hammes et al. Key roles of pH and calcium metabolism in microbial carbonate precipitation. Re/Views in Environmental Science & Bio/Technology 1:3-7 (2002).
Ivanov et al, "Calcite/aragonite-biocoated artificial coral reefs for marine parks", AIMS Environmental Science, Aug. 22, 2017, vol. 4 (4), pp. 586-595.
Ivanov et al., Chapter 7, Biocementation and Biocements. Construction Biotechnol., Green Energy and Technol., Chapter 7, 2017, pp. 109-138.
Jonkers, Henk M., et al., "A Two Component Bacteria-Based Self-Healing Concrete", Proceedings of the 2nd International Conference on Concrete Repair, Rehabilitation and Retrofitting (ICCRRR), Cape Town, South Africa, Nov. 24-26, 2008. Concrete Repair, Rehabilitation and Retrofitting II, pp. 119-120, Taylor & Francis Group, London.
JP2017-566616 Office Action with Search Report dated Oct. 1, 2018 (w/ English translation).
JP2018-242426 Office Action with Search Report dated Feb. 20, 2020 (w/ English translation).
Kalantary et al., Evaluation of the ability to control biological precipitation to improve sandy soils. Procedia Earth. Planet. Sci., 2015, vol. 15:278-284.
Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.
Karthik et al. Properties of Bacterial-based Self-healing Concrete—A review. International Journal of ChemTech Research, vol. 9, No., 2, pp. 182-188 (2016).
Kim et al. Calcium Carbonate Precipitation by Bacillus and Sporosarcina Strains Isolated from Concrete and Analysis of the Bacterial Community of Concrete. J. Microbiol. Biotechnol. (2016), 26(3), 540-548. First published online Dec. 23, 2015.

(56) References Cited

OTHER PUBLICATIONS

Kim et al. Microbially mediated calcium carbonate precipitation on normal and lightweight concrete. Construction and Building Materials, vol. 38, pp. 1073-1082 (2013). Available online Nov. 6, 2012.
KR10-2017-7026519 Office Action dated Apr. 29, 2019 (w/ English translation).
KR10-2017-7026519 Office Action dated Oct. 18, 2018 (w/ English translation).
Kurizaki et al, "A Case of Stone Formation in the Mainz Pouch using Appendix as the Efferent Limb: A Case Report", Nihon Hinyokika Gakkai Zasshi. The Japanese Journal of Urology, 2002, vol. 93(4), pp. 573-576. (English translation of abstract.).
Ibtisam A. Hammad et al., Urease activity and induction of calcium carbonate precipitation by Sporosarcina pasteurii NCIMB 8841; Journal of Applied Sciences Research 9(3): 1525-33, 2013.
Le Metayer-Levrel G, et al, "Applications of bacterial carbontogenesis to the protection and regeneration of limestones in building and historic patrimony," Sedimentary Geology, Jul. 31, vol. 126, No. 1, pp. 26, 29, 32-33 (1999).
Mazria. It's the Architecture, Stupid! pp. 48-51. Retrieved Aug. 29, 2021 from URL: https://backspace.com/notes/images/its_the_architecture.pdf. May/Jun. 2003.
Mendz et al. The urea cycle of Helicobacter pylori. Microbiology 142, 2959-2967 (1996).
Metayer-Levrel et al., Applications of bacterial carbonatogenesis to the protection and regeneration of limestones in buildings and historic patrimony. Sedimentary Geology., 1999, vol. 126: 25-34.
Meyer et al., "Microbiologically-Induced Soil Stabilization: Application of Sporosarcina pasteurii for Fugitive Dust Control", Geo-Frontiers Congress 2011, pp. 4002-4011.
Nemati, M. et al, Modification of Porous Media Permeability, Using Calcium Carbonate Produced Enzymatically In Situ, Enzyme and Microbial Technology, 2003, pp. 635-642, vol. 33, Elsevier.
Park et al., "Effect of Plant-Induced Calcite Precipitation on the Strength of Sand", Journal of Materials in Civil Engineering, 2014, vol. 26, Issue 8.
PCT Search and Patentability Report for PCT/US2016/21763, dated Jun. 2, 2016.
PCT Search and Patentability Report for PCT/US2017/21833, dated Jun. 9, 2017.
PCT/US2011/033920 International Search Report and Written Opinion dated Aug. 2, 2011.
PCT/US2016/021763 International Preliminary Report on Patentability dated Sep. 12, 2017.
PCT/US2016/021763 Written Opinion dated Jun. 2, 2016.
Pedersen et al. Evidence for bacterial urea production in marine sediments. FEMS Microbiology Ecology 12, 51-59 (1993).
Phillips A.J., Biofilm-induced calcium carbonate precipitation: Application in the subsurface. Ph.D., Dissertation, Montana State University, Nov. 2013, pp. 1-241.
Phillips et al., Engineered applications of ureolytic biomineralization: a review. Biofouling, 2013, vol. 29(6): 715-733.
Phua, Y.J., et al., "Morphology and Polymorphism of Calcium Carbonate Precipitated from Different Calcium Sources via Enzyme Induced Carbonate Precipitation", Department of Physics, University of Oslo, Norway, 2016, Goldschmidt Conference Abstracts—1 Page.
Pinar et al, "Bacterial Community Dynamics During the Application of a *Myxococcus xanthus*—Inoculated Culture Medium Used for Consolidation of Ornamental Limestone", Microb.Ecol., 2010, vol. 60, pp. 15-28.
Reddy et al. Embodied energy of common and alternative building materials and technologies. Energy and Buildings, vol. 35, Issue 2, pp. 129-137 (2003).
Remediation of Concrete Using Microorganisms, S.K. Ramachandran et al., ACI Materials Journal Jan./Feb. 2001.
Rodriguez-Navarro, Carlos, et al., "Influence of Substrate Mineralogy on Bacterial Mineralization of Calcium Carbonate: Implications for Stone Conservation", Applied and Environmental Microbiology, Jun. 2012, vol. 78, No. 11, pp. 4017-4029.
Romillac N., Ammonification. Encyclopedia of Ecology, 2nd edition, 2019, vol. 2: 256-263.
Search Report for EP Application No. 16 762 507.8 dated Sep. 28, 2018.
Stabnikov et al., "Immobilization of Sand Dust and Associated Pollutants Using Bioaggregation", Water, Air, & Soil Pollution, 2013, vol. 224, 1631.
Stabnikov, Viktor, et al., "Halotolerant, Alkaliphilic Urease-Producing Bacteria from Different Climate Zones and their Application for Biocementation of Sand", World Journal of Microbiology and Biotechnology, 2013, vol. 29, pp. 1453-1460.
Stocks-Fischer, Shannon et al, Microbiological Precipitation of CaCO3, Soil Biology and Biochemistry, 1999, pp. 1563-1571, vol. 31, Elsevier Science Ltd.
Streamer, M., "Urea and Arginine metabolism in the Hard Coral, Acropora acuminata", Comp. Biochem. Physiol., vol. 65B, pp. 669 to 674, 1980.
Sun et al. Study of magnesium precipitation based on biocementation. Marine Georesources & Geotechnology, 2019, vol. 37, No. 10, pp. 1257-1266. Published online Jan. 29, 2019.
Talaiekhozani et al., "Application of Proteus mirabilis and Proteus vulgaris mixture to design self-healing concrete", Desalination and Water Treatment, 2014, vol. 52, pp. 3623-3630.
The Better Brick, 2010 Next Generation Winner (https://www.metropolismag.com/uncategorized/the-better-brick-2010-next-generation-winner/).
Therkildsen et al., Urea production by the marine bacteria *Delaya venusta* and *Pseudomonas stutzeri* grown in minimal medium, Aquatic Microbial Ecology, vol. 13:213-217 (1997).
Through the Sandglass, (http://throughthesandglass.typepad.com/through_the_sandglass/2010/07/sandbacteriaurinebricks-continuing-performances-of-bacillus-pasteurii.html) Jul. 19, 2010.
T.K. Ghose et al., "Studies on fibre-entrapped whole microbial cells in urea hydrolysis," Enzyme and Microbial Technology, vol. 1, No. 1, pp. 47-50, Jan. 1, 1979.
U.S. Appl. No. 15/066,692 Office Action dated Aug. 15, 2019.
U.S. Appl. No. 15/066,692 Office Action dated Mar. 11, 2019.
U.S. Appl. No. 15/066,692 Office Action dated Oct. 19, 2018.
U.S. Appl. No. 16/781,622 Office Action dated Dec. 24, 2020.
U.S. Appl. No. 16/781,622 Office Action dated Mar. 22, 2021.
Van Paassen et al. Scale up of BioGrout: a biological ground reinforcement method. Hamza et al., ed. Proceedings of the 17th International Conference on Soil Mechanics and Geotechnical Engineering, IOS Press, pp. 2328-2333 (2009).
Van Paassen, Leon A., et al., "Potential Soil Reinforcement by Biological Denitrification", Ecological Engineering, 2010, vol. 36, pp. 168-175.
Vijay et al. Bacteria based self healing concrete—A review. Construction and Building Materials 152:1008-1014 (2017). Available online Jul. 15, 2017.
Wang et al., Application of microorganisms in concrete: a promising sustainable strategy to improve concrete durability. Appl. Microbial Biotechnol., 2016, vol. 100: 2993-3007.
Wei et al. Biomineralization processes of calcite induced by bacteria isolated from marine sediments. Brazilian Journal of Microbiology 46, 2, 455-464 (2015).
Whiffin. Victoria S. et al, Microbial Carbonate Precipitation as a Soil Improvement Technique, Geomicrobiology Journal, 2007, pp. 417-423, vol. 24, Taylor & Francis Group, LLC.
Whiffin, Victoria S., Microbial CaCO3 Precipitation for the Production of Biocement, PhD Thesis, 2004, Murdoch University, Western Australia.
Wikipedia, "Shale," Aug. 22, 2018; retrieved on Sep. 13, 2021 from https://en.wikipedia.org/w/index.php?title=Shale&oldid=855968675.
Wikipedia, "Pseudomonas fluorescens," May 15, 2018; retrieved on Sep. 13, 2021 from https://en.wikipedia.org/w/index.php?title-Pseudomonas_fluorescens&oldid=841444300.
Wiktor et al., Quantification of crack-healing in novel bacteria-based self-healing concrete. Cement & Concrete Composites, 2011, vol. 33: 763-770.

(56) References Cited

OTHER PUBLICATIONS

Yoosathaporn et al., The influence of biocalcification on soil-cement interlocking block compressive strength. Biotechnol. Agron. Soc. Environ.,2015, vol. 19 (3): 262-269.

Zander, R., et al., "Association Between Plasma Ionized Calcium and Lactate Concentration", Intensive Care Medicine, 1993, vol. 19, No. 6, pp. 362-363.

Zeolite as a Binding Agent for Ammonia Ions and as a Soil Additive. Part 1 Amonnia Adsorption by the Zeolite, Proceedings of the 5th Serbian-Croatian-Slovenian Symposium on Zeolites, J. Milovanovic et al., May 2013.

Zeynep Basaran Bundur et al., Biomineralized cement-based materials: Impact of inoculating vegetative bacterial cells on hydration and strength, Cement and Concrete Research 67:237-245 (2015). (Available online Oct. 27, 2014).

Zhao et al., Bioremediation of Cd by strain GZ-22 isolated from mine soil based on biosorption and microbially induced carbonate precipitation. Environ. Sci Pollut Res., 2017, Vo. 24: 372-380.

Co-pending U.S. Appl. No. 18/178,078, inventors Hill; Thomas A. et al., filed Mar. 3, 2023.

Co-pending U.S. Appl. No. 18/178,082, inventor Dosier; Ginger K., filed Mar. 3, 2023.

Ramesh et al. Estimation of porosity values in clay bricks. Int. J. Modn. Res. Revs., vol. 5, Issue 9, pp. 1613-1614 (Sep. 30, 2017).

Taud et al. Porosity estimation method by X-ray computed tomography. Journal of Petroleum Science and Engineering 47 (2005) 209-217.

Co-pending U.S. Appl. No. 18/497,398, inventors Dosier; Ginger K. et al., filed Oct. 30, 2023.

Co-pending U.S. Appl. No. 18/501,579, inventors Thomas; A. Hill et al., filed Nov. 3, 2023.

\* cited by examiner

COMPOSITIONS AND METHODS FOR DUST CONTROL

REFERENCE TO RELATED APPLICATIONS

This application is a continuation-in-part of U.S. application Ser. No. 15/066,692 filed Mar. 10, 2016, which claims priority to U.S. Provisional Application No. 62/200,288 filed Aug. 3, 2015, U.S. Provisional Application No. 62/188,556 filed Jul. 3, 2015, and U.S. Provisional Application No. 62/130,854 filed Mar. 10, 2015, the entirety of each of which is specifically incorporated by reference.

BACKGROUND

1. Field of the Invention

The invention is directed to kits, compositions, tools and methods for dust control. More particularly, the invention is directed to materials and methods for dust suppression, with isolated enzymes, enzyme-producing bacteria or cells, or spores that give rise to enzyme-producing microorganisms.

2. Description of the Background

The built environment is primarily constructed using a limited palette of traditional materials: clay, concrete, glass, steel, and wood. Commonly used throughout history, masonry construction continues to make up a large part of the built environment, utilized for both load bearing structures and veneer construction. According to Chaisson, globally, traditional clay brick manufacturing produces over 1.23 trillion units per annum with a heavy dependency on non-renewable natural resources. Clay brick manufactured in coal-powered kilns emits approximately 1.3 pounds of carbon dioxide per unit. According to Burke, in total, brick manufacturing emits over 800 million tons of man-made $CO_2$ each year, and yet represents only one material currently used in building construction.

Fired clay bricks can be manufactured between 3-20 days, depending on the equipment and processes used. This range represents modern automated factories able to process bricks without manual labor, to the clamp method of bricks stacked around a burning fire used in many developing nations.

As an alternative to load bearing fired clay masonry, Concrete Masonry Units [CMU] are widely used as they are more economical, faster to manufacture and can serve as a structural typology for global construction. Comprised of concrete, these units are made with Portland cement, large aggregate and sand filler. According to Hanley of the United States Environmental Protection Agency, global carbon dioxide ($CO_2$) emissions from cement production were approximately 829 million metric tons of $CO_2$ in 2000.

These traditional materials contain a high-embodied energy, with components of concrete and steel mined from non-renewable resources. Approximately, forty-percent of global carbon dioxide is linked to the construction industry, primarily due to material production and disposal. Biologically grown materials can be pollution free and contain a low embodied energy, if produced as part of a local ecosystem.

Natural cement is created through chemical deposition and chemical processes associated with weathering, and can be found in various locations on the earth's crust. The formation of natural sandstones is primarily attributed to the precipitation of calcite cement. As an alternatively to natural deposition, a form of natural cement has been produced with urease producing *Sporosarcina Pasteurii*, a nonpathogenic, common-soil bacterium has the ability to induce the production of calcite through a chemical reaction. The result is a hardened material formed in a process referred to by Stocks-Fischer as microbial induced calcite precipitation [MICP]. Applications include environmental stabilization of contaminated soils and encapsulation of hazardous and other contaminants in natural soils and acid mine tailings. Ramachandran and Jonkers have proposed the use of microbes to remediate cracks in concrete structures and the repair of cracks in monuments. According to DeJong and Whiffin, civil engineering researchers in the United States, Australia and the Netherlands have proposed the use of MICP for soil stabilization and erosion control.

A need exists for a process to manufacture building materials that does not impose the high energy costs associated with the manufacture of clay bricks and other conventional stone replacement, but utilizes readily available materials and is both economical and environmentally safe.

SUMMARY OF THE INVENTION

The present invention overcomes problems and disadvantages associated with current strategies and designs, and provides new tools, compositions, and methods for the manufacture of building materials.

One embodiment of the invention is directed to compositions comprising a support material to which is coupled urease-producing cells or cell spores and a transport medium and optionally a nutrient mix. Preferably the support material is organic or inorganic and comprises rock, glass (e.g. Poraver), wood, paper, metal, plastic, polymers, minerals or combinations thereof. Preferably the composition is a liquid, a gel, a sludge, a pump-able slurry, a dry powder or crystals and the support material is in the form of beads, grains, rods, strands, fibers, flakes, pulverized or crushed stone, crystals, fines, or combinations thereof. Preferably the support material is sand, glass, wood (e.g., residuals, pulp, sawdust, lignin), metal, polymers, fines (e.g., microcellulose), waste materials (e.g., ash, scrubber waste, residuals), co-cultured microorganisms or combinations thereof and the urease-producing cells or cell spores comprise yeast, algae, bacteria or eukaryotic cells, cell spores, anaerobic cells, or facultative anaerobic cells. Preferred bacteria are *Sporosarcina pasteurii, Bacillus megaterium, Sporosarcina ureae, Proteus vulgaris, Bacillus sphaericus, Myxococcus xanthus, Proteus mirabilis, Helicobacter pylori*, or variants, serotypes, mutations or combinations thereof, and preferred yeast, algae, bacteria or eukaryotic cells or cell spores are genetically engineered. The support material and the cells are preferably coupled via hydrophobic bonds, hydropyllic bonds, ionic bonds, non-ionic bonds, covalent bonds, van der Waal forces, or a combination thereof and/or the support material is at least partially or totally encompassed by a film that promotes binding of the urease-producing cells. Preferred films comprise a polymer or a cell nutrient and preferably the composition contains a coloring agent which may be red, blue, green, yellow or any combination or shade thereof. Preferably the composition contains an identifying agent or a detectable marker such as a microscopic tag, a color, a nucleic acid or peptide, an enzyme or another substance.

Another embodiment of the invention is directed to kits for manufacturing solid forms comprising: the composition of the invention, a second composition containing nutrients for proliferation of the ureases-producing cells and/or germination of the cell spores; a plurality of sets of formworks wherein each set encloses the shape of at least one solid form and contains one or more porous panels; and a third composition comprising a calcium source (e.g., $CaCl_2$), a nitrogen source (e.g., urea) or both a calcium source and a nitrogen source. Preferably the kit is for the creation of solid forms such as, for example, rectangular, square, rounded, oval or an irregular shape. Preferred solid forms include but are not limited to blocks, boards, bricks, pavers, panels, tiles, or veneer. Preferably kits of the invention are for the manufacture of blocks such as, for example, concrete masonry, cinder blocks, foundation blocks, breeze blocks, hollow blocks, solid blocks, besser blocks, clinker blocks, high or low density blocks, or aerated blocks. Preferably the nutrients include amino acids, proteins, polysaccharides, fatty acids, vitamins and minerals.

Another embodiment of the invention is directed to methods for manufacture of solid forms comprising: mixing the composition of the invention with an aggregate material and water to form a mixture, wherein the aggregate material is largely composed of particulates of 5 mm or greater or particles of than 5 mm or less in diameter (e.g., fines); optionally apportioning the mixture into multiple form works wherein each form work contains at least one porous panel; adding a second composition to the mixture, wherein the second composition contains nutrients that promote proliferation of the urease-producing cells; adding a third composition to the mixture, wherein the third composition is a liquid that contains calcium; incubating the mixture for a period of time to form covalent bonds between the particulates; and removing the solid forms from the form works. Preferably the aggregate material comprises rock, glass, wood, paper, metal, plastic, polymers, minerals or combinations thereof, and/or mixing comprising spraying the composition as a liquid onto the aggregate material. Preferably the form works are substantially submerged during the incubating and air is bubbled to the submerged form works. Preferably a third composition is added to the mixture repeatedly during incubating which drains through the bottom panel and, optionally, is recycled. Preferably, incubating is performed under ambient conditions and the third composition contains calcium chloride, calcium acetate, calcium phosphate, calcium carbonate, calcium lactate, calcium nitrate, or a calcium salt. Preferably the pH of the mixture is monitored during the incubating. Preferably the solid forms are blocks, boards, bricks, thin bricks, pavers, panels, tiles, or veneer, stone (manufactured, cultured, colored), and the mixture further contains fibers or nanofibers that are, for example, fibers or nanofibers of wood, glass, plastic, metal or a polymer. Preferred fibers include, for example, polypropylene, HDPE, carbon fibers including high-strength carbon fibers, rayon, and biodegradable and non-biodegradable fibers such polymers of, for example, poly lactic acid, fibers of cellulose, minerals, chitin, lignin, and other plant materials. Preferably additional nutrients are added during incubating and the solid forms removed from the form works are dried.

Another embodiment of the invention comprises compositions containing urease producing cells or cell spores that are encapsulated or coated with nutrient media such as, for example, proteins or polysaccharides, or polymers such as poly lactic acid which is water soluble. Preferably the nutrient media further contains additional urease producing cells or cell spores.

Another embodiment of the invention comprises methods of dust control comprising: providing two compositions, wherein one composition contains an aqueous or dry mixture of viable cells or spores of urease-producing microorganisms and a transport media, and the other composition contains an aqueous form of calcium, wherein either or both compositions further contain urea and ingredients for growth of the microorganisms; and separately applying the two compositions to an area. Preferably the microorganisms comprise yeast, algae, bacteria, eukaryotic cells, or recombinantly engineered microorganisms, and also preferably the bacteria comprise *Sporosarcina pasteurii, Bacillus megaterium, Sporosarcina ureae, Proteus vulgaris, Bacillus sphaericus, Myxococcus xanthus, Proteus mirabilis, Helicobacter pylori*, or variants, serotypes, mutations, or combinations thereof. Preferably the transport medium maintains viability without promoting significant propagation of the microorganisms and may comprises minimal cell medium. Preferably the calcium comprises calcium chloride, calcium acetate, calcium phosphate, calcium carbonate, calcium lactate, calcium nitrate, and/or a calcium salt, and the ingredients for growth comprise one or more of water, nutrients, vitamins, minerals, amino acids, proteins, oils, fatty acids, saccharides and polysaccharides. Preferably methods of applying comprise spraying or misting and the area is a walking path, a mining area, tailings, gangue, a debris or waste pile, a cliff, a roadway, an aircraft landing area, a contaminated or hazardous area, or a construction site, or air space of a mining area, factory, manufacturing plant, or work area. Preferably, either or both compositions form a film on a surface that promotes binding of the microorganisms and may be aqueous. Also, the film may comprise a polymer, and either or both compositions may contain a coloring agent, or a detectable marker. Applying may comprise repeated applications of either or both compositions to the surface, and/or further applying another aqueous composition to the area.

Another embodiment of comprises kits for dust control comprising: a first composition containing a mixture of viable cells or spores of urease-producing microorganisms and a transport media; and a second composition containing a form of calcium, wherein either or both first and second compositions further contain urea and ingredients for growth of the mixture of viable cells or spores. Preferably the mixture of viable cells or spores comprise yeast, algae, bacteria, eukaryotic cells, or recombinantly engineered microorganisms, and preferably the bacteria comprise *Sporosarcina pasteurii, Bacillus megaterium, Sporosarcina ureae, Proteus vulgaris, Bacillus sphaericus, Myxococcus xanthus, Proteus mirabilis, Helicobacter pylori*, or variants, serotypes, mutations, or combinations thereof. Preferably the transport medium maintains viability without promoting significant propagation of the microorganisms, such as minimal cell medium. The form of calcium may comprise calcium chloride, calcium acetate, calcium phosphate, calcium carbonate, calcium lactate, calcium nitrate, and/or a calcium salt, and the ingredients for growth of microorganisms comprise one or more of water, nutrients, vitamins, minerals, amino acids, proteins, oils, fatty acids, saccharides and polysaccharides. Preferably either or both first and second compositions are aqueous, may further contain a polymer, a coloring agent, and/or a detectable marker. Kits may also comprise an apparatus for applying either or both first and second compositions.

Other embodiments and advantages of the invention are set forth in part in the description, which follows, and in part, may be obvious from this description, or may be learned from the practice of the invention.

DESCRIPTION OF THE INVENTION

Traditional constructions materials such as clay bricks and concrete require enormous amounts of energy during the manufacture process. These processes are heavily reliant on burning natural resources such as oil, coal and wood. This reliance results in the consumption of massive amounts of energy resources and equally massive carbon dioxide emissions, thus a great dependency on limited energy sources. An alternative has been described which requires much less energy for manufacturing that utilizes enzymes produced by microbial cells. Typically, cells are aerobic and/or facultative anaerobic cells and include, for example, *Sporosarcina pasteurii, Bacillus megaterium, Sporosarcina ureae, Proteus vulgaris, Bacillus sphaericus, Myxococcus xanthus, Proteus mirabilis, Helicobacter pylori* and other strains, serotypes, variations, mutations and CRISPR modifications (clustered regularly interspaced short palindromic repeats). Cells produce the enzyme urease which, in the presence of calcium and nitrogen sources, forms calcite crystals. The process is generally referred to a microbial induced calcite precipitation (MICP), which can be performed with the cells or purified enzyme. As little to no heating is necessary, the energy savings in both expenses and efficiency is enormous.

The enzymes and/or the enzyme-producing cells are dispersed in a composition containing a nitrogen source and a calcium source, such as for example, urea, and calcium chloride with an aggregate material catalyzing the production of ammonia and carbon dioxide, increasing the pH level of the composition. The rise in pH forms a mineral precipitate combining calcium with carbon dioxide. The cells or other particles act as nucleation sites, attracting mineral ions from the calcium to the particle surfaces forming calcium carbonate crystals such as calcite crystals or other calcium carbonate polymorphs. The mineral growth fills gaps between the particles of aggregate, bio-cementing or bonding aggregate particles forming a solid. The resulting material exhibits a composition and physical properties similar to naturally formed sandstone, but whose hardness can be predetermined based at least on the structure of the initial components and the pore size desired.

Compositions and methods have been surprisingly discovered that are useful in the control of dust. The compositions include two solutions, a first solution containing a fluid plus urease enzyme or urease-producing cells or cell spores and a second aqueous solution containing calcium ions. The first or second solution may contain nutrients for the propagation of the cells or the spores, a nitrogen source such as, preferably urea, and a carrier such as clay or pond fines. Commercial sources of urease enzyme include, for example, jack beans. The enzymes can be maintained as a liquid, but are preferably lyophilized for ease of storage and transport, and re-hydrated before use with a fluid such as, preferably, water, buffered water, or another hydrating agent that preserves enzyme activity. Preferable, pure enzyme is encapsulated in carbohydrate, lipid or other polymer microshells or spheres. Encapsulation techniques include, for example, encapsulation in nanoorganized microshells, and encapsulation in xanthan-alginate spheres. Preferred enzyme concentrations are from 0.5-5 mg/ml in 0.1 M phosphate buffer, pH 7.6. Preferably enzyme concentrations are from about 0.1 to 100 mg/ml, more preferably about 0.5 to 3.0 mg/ml, more preferably from about 0.5 to 2.0 mg/ml, and more preferably about 1.0 mg/ml. Enzyme can be further diluted prior to use to obtain a rate of 0.02-0.04 AA/minute. Enzyme activity can be measured by the reaction:

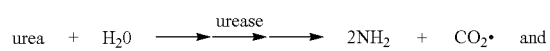 and

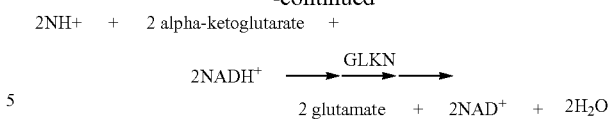

which couples ammonia production to a glutamate dehydrogenase reaction. Accordingly, one unit of enzyme results in the oxidation of one micromole of NADH per minute at 25° C. and pH 7.6.

This method for manufacturing construction materials through induced cementation exhibits low embodied energy and can occur at ambient pressures or higher or lower, and ambient temperatures or higher or lower. For example, preferred pressures are from about 10 psi to about 100 psi and all pressure values in between, also preferred at from about 14 psi to about 50 psi. Although higher pressures can be utilized, there is generally no need for the energy expense required. Preferred temperature ranges are from at least minus 20° C. to above 80° C., preferably from about 5° C. to about 50° C., preferably from about 15° C. to about 30° C., preferably from about 20° C. to about 25° C. Preferably, temperature ranges are below 30° C., below 40° C., below 50° C., below 60° C., or below 70° C. The ambient temperatures and conditions as well as the content of available aggregates can determine whether pure enzyme, lyophilized enzyme, spores, or live cells are utilized as the starting components. Living cells can be used in temperatures where mild weather conditions exist, whereas pure enzymes can be advantageous at more extreme conditions of cold or heat. Spores are used when immediate calcification is not required and the spores are provided sufficient time to germinate and express enzyme.

Processing also involves the production of quantities of by-products such as ammonia, not all of which is utilized in calcite formation. It is another embodiment of the invention to include an effluent recovery system in association with the production methodology. The recovery of ammonia from effluent converts the effluent to plain water which can be recycled or disposed of without any need for additional decontamination procedures. Preferred ammonia recovery methodologies include, for example, ion-exchange resins and commercially available processing such as Ammonia Electrolysis, zeolite, clinoptilolite and combinations thereof. Preferably, the ammonia recovered can be utilized in fertilizers, converted to nitrogen, utilized for energy generation or utilized for other applications.

One embodiment of the invention is directed to compositions comprising urease-producing cells or cell spores, urease enzymes (e.g., crude extract, or unpurified or purified enzymes) in a transport medium and optionally a nutrient medium. Transport medium includes, for example, growth media for urease-producing and/or other supporting cells, enzyme stabilizing media, reagent media, buffered solutions and combinations thereof. The composition may include or be combined with a support material which may be organic or inorganic and is preferably a solid or semi-solid and preferably contains holes or perforations and/or is otherwise porous. Organic support material includes, for example, biomass such as, preferably, moss, hay, straw, grass, sticks, leaves, algae, dirt, ash, dust, particulate material, refuse and combinations thereof. Inorganic material includes, for example, minerals, supplemental cementitious materials (SCM), pulverized or crushed rock, fines, and combinations thereof. Fibrous materials include sheets or tarps of burlap, paper, wood (e.g. residuals), cotton, or another natural or synthetic fiber. Non-natural and manufactured materials may also be used such as, for example, sheets of plastic, glass, fiberglass, vinyl, rubber, synthetic fabrics or combinations thereof. To the solid support is applied or otherwise introduced urease-producing cells, urease enzyme or simply other cells. Preferably these other cells would be useful to support the grown of the urease-producing cells or enhance the chemical processes involved and not otherwise interfere with the MICP process or to act as nucleation sites. Preferably these other cells are native or latent microorganisms in the local environment or provided with the mix, non-pathogenic, non-toxic and/or relatively harmless at the amount used, and easily obtained, present in the local environment or provided. Cells can be proliferated directly on the support material and, at a desired density or growth stage, the organic material evenly dispersed and/or thoroughly mixed into an aggregate material for manufacture of construction tools and products. Inorganic materials that can be used include, for example, rock (e.g., fines), sand, glass, wood, paper, metal, plastic, polymers, minerals, manufacturing or processing waste materials such as ash, carbon or wood residuals, any of which can be crushed or used whole or combinations thereof. Compositions may also be formed from waste materials that are otherwise hazardous (e.g., radioactive materials, materials with dangerous metal or poison content, contaminants from scrubbers, or other harmful materials) and formed into solid structures that can be stably stored or otherwise safely disposed.

Compositions of the invention may be sprayed or otherwise applied to sheets or mats or natural or non-natural materials and the sheets used, for example, to prevent erosion by formation of a calcium carbonate crust over a surface, a pile, a cliff or other structure that's subject to erosion. With the use of perforated or porous sheets or mats, the crust forms through the support material attaching the material on which the sheet has been placed. Nucleation sites for calcite formation can include, for example, polymers, fibers, fines, SCM, added Portland cement, powders, co-cultivated microorganisms, and combinations thereof. One or multiples layers of crusts can be formed on site. In this way, erosion and dust control can be substantially reduced or eliminated in defined areas. Importantly, in this fashion the sheet can be easily replaced over time and/or a fresh composition of the invention re-applied to the surface as needed or as desired. Mats provide the additional benefit of "seeding" the site for rehabilitation once operations have ceased—thereby allowing site recovery efforts to proceed such as returning the site to a natural state. This is especially applied to mining sites in which mining operations have ceased. Preferred areas for application include a walking path, a mining area, tailings, gangue, a debris or waste pile, a cliff, a roadway, an aircraft landing area, a contaminated or hazardous area, or a construction site, or air space of a mining area, factory, manufacturing plant, or work area.

In a preferred embodiment of the invention, compositions of the invention are applied to a surface area as a liquid, a gel, a slurry, a sludge, a semisolid or a dry powder. Spores and/or microorganisms of a composition of the invention produces enzymes that catalyze formation of a crust of calcium carbonate in the presence of liquid, which is preferably water, buffered water or another aqueous material. A nutrient mix suitable for the particular microorganism can be included with the cells. When the composition dries, the crust remains and cells go dormant. As cells self-propagate, provided sufficient nutrients and/or substrate materials are present, new crust will form whenever sufficient aqueous liquid is provided. In a preferred embodiment, nutrients and/or substrate materials may be distributed over the surface area of interest in slow-release or timed-release form such as dry components with a pre-determined rate of dissolution. Reformation may simply be a matter of re-applying water that dissolves nutrient and/or substrate thereby re-activating the microorganisms. The re-activated microorganisms produce enzyme that forms crust. This process can be repeated with or without the reapplication of microorganisms, nutrients and/or substrates, or with only occasional additions. This process may be coupled with weather events so that the rain provides the source of water. By providing a composition that provides microorganisms and/or spores and contains slow-release nutrients and/or substrate, crust can be reformed over an area repeatedly over long periods of time.

Preferably compositions of the invention including all necessary components such as microorganism, spores and/or enzymes, a nitrogen source, and a calcium source and optionally nucleation sites (e.g., powders, fines, co-cultured microorganisms and/or other materials), are applied to a surface, such as, for example, a dirt road, or a structure such as a hill or cliff. Microorganisms proliferate and produce enzyme which h catalyzes the formation of a crust of calcium carbonate over the road surface. As vehicles travel over the road, the crust breaks eventually turning the crust into dust. Periodically the geographic region experiences rain or other forms of precipitation that dissolves slow-release nutrients and/or substrate materials, thereby promoting proliferation of dormant microorganisms. The microorganisms produce enzymes which catalyze new crust formation over the road. In periods of reduced precipitation, an aqueous solution is re-applied to the road to activate the microorganisms which may or may not contain additional nutrients and/or substrate materials. Preferably the composition is a liquid, a gel, a slurry, a sludge or dry powder and the support material may be in the form of beads, grains, rods, strands, fibers, flakes, dirt, biomass, sand, pulverized or crushed stone, fines, supplemental cementitious materials (SCM), crystals, co-cultivated microorganisms, or combinations thereof. Fines sizes are preferably equal to or less than 250 micron, more preferably equal to or less than 200 micron, more preferably equal to or less than 150 micron, or more preferably equal to or less than 100 micron (reference examples include micron size of beach sand=700, micron size of fine sand=250; micron size of Portland cement=74; micron size of silt=44; micron size of smoke=2). Support material and aggregate material can be the same or different. Preferably the support or aggregate material is sand, glass, metal, added Portland cement, SCM, fines, co-cultivated microorganisms (e.g., native, latent, local, added, or genetically modified microorganisms), or combinations thereof and the urease-producing cells or cell spores comprise yeast, algae, anaerobic cells, facultative anaerobic cells, bacteria or eukaryotic cells or cell spores. Preferred bacteria are *Sporosarcina pasteurii, Sporosarcina ureae, Proteus vulgaris, Bacillus sphaericus, Myxococcus xanthus, Proteus mirabilis, Helicobacter pylori*, or variants, serotypes, mutations or combinations thereof, and preferred yeast, algae, bacteria or eukaryotic cells or cell spores are genetically engineered. Other enzyme producing bacteria that are capable of biocementation include *Sporosarcina ureae, Proteus vulgaris, Bacillus sphaericus, Myxococcus xanthus, Proteus mirabilis* and *Helicobacter pylori*, although proper concerns should be given to pathogenic strains. Combinations of any of these strains as well as functional variants, mutations and genetically modified stains may be used as well. The support material and the cells are preferably coupled via hydrophobic bonds, hydropyllic bonds, ionic bonds, non-ionic bonds, covalent bonds, van der Waal forces, or a combination thereof and/or the support material is at least partially or totally encompassed by a film that promotes binding of the urease-producing cells. Preferred films comprise a polymer or a cell nutrient and preferably the composition contains a coloring agent which may be red, blue, green, yellow or any combination or shade thereof. Preferably the composition contains an identifying agent or a detectable marker such as a microscopic tag, a color, an enzyme or another substance.

Support materials and/or aggregate materials may contain additional components that provide an advantage to the construction materials. For example, chemicals and/or additional cells (e.g., native, local or latent bacteria, yeast, eukaryotic cell, algae, and recombinant variations thereof), can be included that produce enzymes, cofactors and/or other chemicals useful in breaking down stains in and/or acquired by the final product and/or additional nucleation sites. Stains include stains from air pollution, soot, mold or animal waste products. Alternatively, the chemical or enzymes may impart color, texture or a desired function or appearance to the final product.

Another embodiment of the invention is directed to kits for manufacturing solid forms comprising: the composition of the invention, a second composition containing nutrients for proliferation of the ureases-producing cells and/or germination of the cell spores; a plurality of sets of formworks wherein each set encloses the shape of at least one solid form and contains one or more porous panels; and a third composition comprising a calcium source (e.g., $CaCl_2$), a nitrogen source (e.g., urea) or both a calcium source and a nitrogen source. Preferably the kit is for the creation of solid forms such as, for example, rectangular, square, rounded, oval or an irregular shape. Preferred solid forms include but are not limited to blocks, boards, bricks, pavers, panels, tiles, counter tops, or veneer. Preferably kits of the invention are for the manufacture of blocks such as, for example, concrete masonry, cinder blocks, foundation blocks, breeze blocks, hollow blocks, solid blocks, besser blocks, clinker blocks, high or low density blocks, or aerated blocks, thin bricks, manufactured stone, cultured or colored stone. Nutrient compositions of the invention may contain nutrient media to maintain and/or allow the cells to flourish and proliferate. The various types of nutrient media for cells, and in particular, bacterial cells of the invention are known and commercially available and include at least minimal media (or transport media) typically used for transport to maintain viability without propagation, and yeast extract, molasses, and corn steep liquor, typically used for growth and propagation. Preferably the nutrients include amino acids, proteins, polysaccharides, fatty acids, vitamins and minerals.

Another embodiment of the invention is directed to methods for manufacture of solid forms comprising: mixing the composition of the invention with an aggregate material and water to form a mixture, wherein the aggregate material is largely composed of particulates of less than 5 mm in diameter (e.g. less than or about 4 mm, less than or about 3 mm, less than or about 2 mm, or less than or about 1 mm); apportioning the mixture into multiple form works wherein each form work contains at least one porous panel; adding a second composition to the mixture, wherein the second composition contains nutrients that promote proliferation of the urease-producing cells; adding a third composition to the mixture, wherein the third composition is a liquid, powder or paste that contains calcium; incubating the mixture for a period of time to form covalent bonds between the particulates; and removing the solid forms from the form works. Alternatively, the compositions may be combined and added together to the material within the form works or combined with the material prior to addition to the form works.

Another embodiment of the invention is directed to the structure and composition of form works. Preferred form works comprises a thermoplastic material that can be molded or extruded into a desired shape. Preferred thermoplastics include, but are not limited to plastics such as polypropylene, polystyrene, polyethylene including HDPE (high density polyethylene), LPDE and reclaimed LDPE (low density polyethylene), and cross-linked polyethylene, glass and most any formable polymer. Preferably, the polymer material is provided as pellets or lens shapes that range in thickness and uniformity. The pellets are filled in a porous mold and steamed under pressure (the mold is not under pressure, pressure just from the steam). The resulting product provides a designed flow directional material, and changes to the gradation impact the flow direction, speed and retained saturation.

Another embodiment of the invention is directed to compositions and structures that do not require formworks (e.g. frameless manufacturing) wherein structures are formed from a combination of the components of the invention plus polymers and/or thermoplastics that are compressed with a compaction device and retain the desired structure. Preferred compression devices include hydraulic presses and preferred pressures are 100 psi or greater, 250 psi or greater, 500 psi or greater, 1000 psi or greater, 2000 psi or greater, 3000 psi or greater, 4000 psi or greater, 5000 psi or greater, Preferred components of the invention include all the components to form calcium carbonate structures in the form of a sludge or paste. The compaction device compresses the components with added pressure into a form that is maintained and dries without significant alterations of the resulting form. Preferred polymers and thermoplastics include, but are not limited to plastics such as polypropylene, polystyrene, polyethylene including HDPE (high density polyethylene), LPDE and reclaimed LDPE (low density polyethylene), and cross-linked polyethylene, glass, carbohydrates such as starches, lignin, and most any formable polymer. Compressed form can be generated rapidly from a think slurry or sludge and maintains its shape during calcite formation. Preferably calcite formation is accomplished in vapor chambers (e.g., at greater than ambient pressures) that contain increased vapor pressures or are sprayed or misted, wherein the vapor, mist or spray preferably comprises nutrients or chemical substrates. Preferred forms include blocks, bricks, thin bricks, manufactured or cultured stone, pavers, or any useful structure.

Preferably the multiple form works or compression devices create 5, 10, 50, 100, 500, 1,000, 10,000, 100,000 1,000,000 or more forms at a time. The number of form works or compression devices that can be simultaneously utilized is limited only by the complexity of the mechanics and space available. These form works or devices may be stacked or provided in a single layer or pallet. Formwork may have vertical walls which are connected together forming cavity there between to receive the aggregate material. Formworks may also have a floor and, alternatively, the bottom of the formwork may be left open if supported by a porous surface such as soil, or aggregate and composition may be mixed and pressed into molds or extruded. Preferably, vertical walls are at least the inside surfaces thereof, are made of a non-reactive, non-porous material or coating such as cast or extruded acrylic resin. This enables one to easily remove the construction material or the brick from the formwork after it has solidified. In addition, the vertical walls and floor of formwork or pressure devices may have designs that form surface textures in the resulting bricks or other structures (e.g., lines, circles, waves, groves, sketches, images, etc.).

Preferably the aggregate material comprises rock, glass, fiberglass, wood (residuals, pulp, sawdust, lignin), biomass, paper, metal, plastic, polymers, rubber, imitation rubber, vinyl, minerals, co-cultured microorganisms, waste materials (e.g., ash, carbon, scrubber waste, radioactive pellets) or combinations thereof, and/or mixing comprising spraying the composition as a liquid onto the aggregate material. Preferably the form works are substantially submerged during the incubating and air is bubbled to the submerged form works. Preferably a third composition is added to the mixture repeatedly during incubating which drains through the bottom panel and, optionally, is recycled. Preferably, incubating is performed under ambient conditions and the third composition contains calcium chloride, calcium acetate, calcium phosphate, calcium carbonate, calcium lactate, calcium nitrate, or a calcium salt. Preferably the pH of the mixture is monitored during the incubating. Preferably the solid forms are blocks, boards, bricks, pavers, panels, tiles, or veneer, and the mixture further contains fibers or nanofibers that are, for example, fibers or nanofibers of wood, glass, plastic, metal or a polymer. The solid forms can be partially or uniformly porous containing a network of holes or gaps. Holes can be of a predetermined size and/or structure such as, for example, at least 5 microns, at least 10 microns, at least 20 microns, or at least 50 microns in diameter. Alternatively, solid forms can be manufactured with materials that provide virtually no or few holes. For example, adding a non-porous material to the aggregate mixture can create complex and extended pathways that render the form impermeable to fluids.

Another embodiment of the invention comprises compositions containing urease producing cells or cell spores that are coated with nutrient media. Preferably the nutrient media further contains additional urease producing cells or cell spores, and/or nutrients to promote the proliferation of additional cells that have been added to the aggregate that are beneficial to the final product.

Another embodiment of the invention is directed to compositions, methods and systems for the treatment of aggregate materials comprised of particles with a composition comprising one or more of a nitrogen source such as for example urea, a calcium source (e.g., calcium ions) and urease or urease producing cells. Preferably particles have a diameter (e.g., actual, average or effective diameter) of about 50 mm or less, preferably about 25 mm or less, preferably about 20 mm or less, preferably about 10 mm or less, and preferably about 5 mm or less. In one preferred embodiment, aggregate material can also be about 1 mm or less and preferably about 0.5 mm or less, more preferably about 0.1 mm or less, and more preferably about 50 µm or less. Especially preferred particles sizes include from about 10 µm to about 1 mm, from about 100 µm to about 0.5 mm, from about 200 µm to about 1 mm, from about 1 µm to about 200 µm, from about 10 nm to about 1 µm, and from about 10 nm to about 40 nm, and various combinations thereof. Particles include, for example, spores, carbon dust, dust or soot from cement or brick manufacture, cement block manufacture, foundry operations, grinding limestone, sand tailings, mining, smelters, paint manufacturing and byproducts of other manufacturing processes such as slag. Particles may be obtained and collected from available or implemented dust control procedures. Particles may be of mixed sizes including but not limited to sizes equal to and greater than preferred sizes, particles equal to and less that preferred sizes, and combinations of preferred sizes and mixtures thereof. Particles that are aggregates and more sizable particles may include recycled and/or recyclable materials. The nitrogen source of the composition may be a single chemical, such as urea of any grade and purity and is preferably commercially obtained. Calcium ions are preferably obtained from commercially available sources such as, for example, calcium chloride. Urease enzyme or urease-producing bacteria may be included in the composition. Urease-producing bacteria include, but are not limited to the bacteria *Sporosarcina pasteurii, Sporosarcina ureae, Proteus vulgaris, Bacillus sphaericus, Myxococcus xanthus, Proteus mirabilis, Helicobacter pylori* and combinations thereof. Urease producing cells includes non-viable cells that contain enzyme such as, for example, mycells, cells composed of lipids or fatty acids, and cells containing urease. Urease and/or urease-producing cells may produce or release a predetermined amount of enzyme over a defined period of time. Preferably, the amount of urease released per cell is sufficiently rapid to allow for the rapid creation of calcium carbonate in the presence of nitrogen and calcium ions.

Preferably, particles are combined with a nitrogen source (e.g., urea), urease and/or urease producing cells, calcium ions and preferably water to create a homogenous slurry. The slurry can be painted or sprayed onto objects and/or surfaces creating a layer or crust, molded into forms that solidify into objects which may be complete or partially solid, or otherwise pooled for immersion or dipping of objects to be coated with the slurry material again creating layers or a crust over the object surfaces. Objects may contain one or more layers as desired, and layers may be permeable or impermeable to water or improve resistant to wear from weather conditions such as sun damage, snow, ice and rain. Slurries that provide increased resistance are preferably composed with aggregate materials that are particles of less than 0.1 mm diameter. As the liquid dries, calcium carbonate bonds form between the particles and/or the particles and the object. The result can be an object containing an outer shell of hardened calcium carbonite or a formed structure. Objects that can be manufactured according to the invention and/or layered with a crust or coating of the invention include, but are not limited to bricks, cement blocks, pavers, counter tops, glass, fiberglass, polymer and acrylic structures, siding, walls, yard art, slate and rock structures, tiles, paving stones, steps, roofing material, gutters, cement walls and planks, patios, balconies, fencing and combinations thereof.

Another preferred embodiment of the invention comprises producing ammonia and/or other compounds (e.g., ammonia, organic acids, alcohols, phenolics, sulfides) by fermentation of microorganisms (e.g., microorganisms that produce ammonia monooxygenase, hydroxylamine oxidoreductase, nitrifying bacteria). Preferably microorganisms are selectively cultured to maximize generation of the desired enzymes. Hyper-ammonia producing microorganisms include, for example, ruminant-derived microorganisms, intestinal microorganisms, *Peptostreptococcus* sp., *Clostridium* sp., *Calliandra* sp., *Atopobium* sp., *Desulfomonas* sp., and the like. Isolated ammonia can be recycled or utilized in other processes such as in fertilizers and energy production.

Another embodiment of the invention comprises spraying the slurry of the invention onto a natural geological or man-made surface such as a cliff, a dune, an aggregate pile, a ledge, a supporting wall, ores, a foundation, minings, tailings, piles of waste materials from a manufacturing process, construction site, or another structure for which additional support or structuring is desired. Such support is advantageous in convenience and financial considerations as compared to providing additional support of the structure of interest with convention building systems. In addition, and preferably, slurry of the invention can be provided to geological surfaces such as soil around buildings to provide building support, erosion suppression, prevention and/or repair of sink holes, or to create foundation structures to provide solid support and/or stabilization of buildings and other structures, and combinations thereof.

Another embodiment of the invention is directed to compositions, methods and systems comprising a slurry of one or more of water, a nitrogen source (e.g., urea), optionally a calcium source (e.g., $CaCl_2$), and urease or urease-producing cells, but without the addition or any aggregate material such as, for example, without sand, soil, dust, silt or other particles as aggregate materials. Preferably the slurry contains at least water, a nitrogen source (e.g., urea), optionally a calcium source (e.g. $CaCl_2$), and urease or urease-producing microbes, which may include microbial nutrients as appropriate. Preferably the calcium source is provided is another composition and the slurry is calcium-free. This liquid slurry is sprayed, painted, or otherwise placed directly on or in an aggregate material, or formed in a mold of most any shape or structure containing aggregate material, optionally followed by application of the calcium composition. The combination of the aggregate and the aforementioned slurry forms a solidified object, covering or layer (or multiple layers), such as, for example, as a building foundation, a molded object, a layer covering an object, or another desired form. One of the advantages of this technique is that aggregate material does not need to be shipped and there is a concomitant associated savings. Preferably aggregate material is immediately available on site or locally available within an acceptable distance. The addition of the slurry to the already-present aggregate creates a solid or more hardened form of a structure efficiently in situations where transporting or otherwise moving aggregate materials would be difficult, inefficient or impractical such as but are not limited to situations involving creation of, repair of or to further support building foundations and other repairs.

Another embodiment of the invention is directed to compositions and method comprising a slurry of the invention combined with an aggregate material, further containing multiple solid structures that are either hollow or otherwise of lighter weight than the aggregate material. The resulting structure containing the additional objects produce solid objects of lighter weight than objects made of only aggregate material and slurry. Alternatively, it may be desirable to increase the weight of the object by adding objects that are heavier than the aggregate material. Such heavier objects include, but are not limited to rebar or remesh, metal forms, strengthening material and other heavier materials. These additional objects include, but are not limited to plastic, wood, steel, metal, polymer, rods, balls geometric structures, which may be solid, perforated or hollow. Alternatively, the additional objects may be included that have aesthetic properties such as, for example, predetermined colors, materials, functions, properties and designs. This is advantageous when light weight objects are desired, wherein the structure retain sufficient strength for the intended purpose such as, for example, a specific desired compression strength, tensile strength, yield strength, ultimate strength, Young's modulus, elastic modulus, elastic strength, stiffness, hardness, toughness, stress resistance, and combinations thereof.

Another embodiment of the invention is directed to compositions, methods and systems comprising a variety of substrates combined with a slurry of the invention. The addition of sand, fines, silt, or dust (which are lighter and have smaller particles than soil or other aggregates) to urea, urease, optionally calcium and water create lighter structures with equivalent or nearly equivalent support strengths. Preferably the slurry is largely calcium free and a calcium-containing composition is provided in a second application. Advantages of lighter structures include a lower cost of production and a higher efficiency of production, as well as other benefits such as efficiency or manufacture and formation of structures. Preferably, urease enzymes are used to increase the solidification of the structure as compared to the use of enzyme-producing cells. In addition, enzymes are smaller in molecular structure than cells and will pass through smaller pore sizes of aggregate materials having small pore sizes. Also in addition, one or more chemical or compounds can be included to increase the density and/or weight of the liquid composition so that compositions settles quickly or are sufficiently sticky to a surface (e.g., as a gel, foam or semi-solid).

Another preferred embodiment of the invention comprises composition, systems and methods for forming solid or porous solid structures according to the invention that are lighter in weight as compared to convention structures composed of clay or cement. Preferably, the invention comprises creating a spatial gap within the solid structure during manufacture as the structure hardens. This gap can be in the form of holes, tubes, bubbles, or any other three-dimensional shape. A pre-formed shape made of the same aggregate material or materials, or of a different, preferably lighter material can be immersed into the wet, un-hardened slurry of the invention either with or without aggregate material. When the slurry fully formed around that desired shape, the resulting object will weigh less than conventionally prepared objects, such as, for example, clay bricks, cement blocks, pavers, stone composites, or another solid structure composed of one or more aggregate materials. The resulting solid object has an increased strength, new or enhanced aesthetic or performance characteristic, additive or a combination thereof.

Another preferred embodiment of the invention comprises composition, systems and methods for forming protective layers or coverings to solid structures. Preferably the slurry of the invention fills and closes pores in the solid structure (e.g., a fabric impregnated with one or more of microorganisms, nutrients, substrate materials, nucleation sites) so as to provide effective barriers to liquids (e.g. water), gasses (e.g. pollution) or other substances that may impregnate or contaminate a solid structure. Such compositions can be used for erosion control and structural support.

Another embodiment of the invention comprises compositions, systems and method for dust control of, for example, walking paths, piles, aircraft runway, taxi ways, and parking areas, cliffs, vehicle roadways and other large surfaces. Slurries of the invention can be substituted for oils and other dust control compositions presently used on dirt, gravel and other road surfaces to minimize the amount of dust created from vehicles. Slurries of the invention can be sprayed or vaporized from trucks or other vehicles as a liquid, or administered (e.g., spraying) as a dry composition to be activated when wetted, onto surfaces forming a hardened crust to the road or other surface. Slurries comprising substrates and living urease-producing microbes plus nutrients cover road surfaces with a self-renewable crust. An initial application can include microorganisms and optionally included with subsequent applications which may only contain substrate materials. As vehicles pass over the road, the crust may be damaged from the weight of the vehicle, but a crust is recreated and repaired by the presence of the living-slurry. Preferably slurry of the invention for dust control contains no aggregate or only aggregate of 0.5 mm or less in diameter.

Another embodiment of the invention comprises adding slurry of the invention, either with or without aggregate, to conventional procedures for the manufacture of construction materials such as, for example, clay brick, cement blocks, pavers, and other substances. Slurry additions can be included as desired at from 0.0001 percent to 99 percent of the dry weight of the resulting product or empirically determined from the type of aggregate used. Preferably the slurry addition by dry weight is from 1 to 50 percent, from 2 to 75 percent, from 30 to 60 percent, from 25 to 80 percent, from 10 to 25 percent or any combination there.

Another embodiment of the invention comprises creation of a slurry of the invention with which will solidify at a predetermined time. Preferably, slurries contain a predetermined amount of nitrogen and calcium sources as substrates and a predetermined amount of enzyme that solidifies within a desired time frame. Solidification conditions may include the temperature of use, which can be included in the calculations to determine solidification times preferably experimentally or empirically.

The following examples illustrate embodiments of the invention, but should not be viewed as limiting the scope of the invention.

EXAMPLES

Example 1

Reducing dust of surface mining sites is required by MSHA (mining version of OSHA) regulations. Current methods used in the industry include the use of various polymers or chemicals, with the most common being the continuous spray application of water, oils and other dust control liquids. The objective for surface mine dust control is to make fine dust (a byproduct of aggregate mining) heavier than air to prevent respiratory and visibility hazards. According to the invention, micro-organisms are applied either with a nutrient and/or transport material or in association with any conventional treatment for such dust control and/or surface cementation and include production of a calcite cement ($CaCO_3$) in combination with urea (nitrogen/carbon) and a calcium source. Cells and/or nutrient materials are included with an initial application, and optionally with subsequent or follow-on applications. Preferably, applications are of light-weight materials that are quick to cement using the same strains of urease-producing bacteria as used in the formation of bricks, pavers and other solid forms. Alternatively, cyanobacteria, a photosynthetic microorganism that fixes nitrogen from the atmosphere, is substituted for or used in addition to urease-producing bacteria, which reduces nutrient input needs.

Example 2

Recovery systems seek to address: (a) returning effluent to a viable state to be re-used as influent (water becomes a capital expense rather than a consumable material), and (b) the extraction of commercially valuable byproducts from the effluent stream. Preferably, the biocementation process of the invention is useful for the primary production of by-products as products such as, for example, using urease producing microorganisms for the manufacture of ammonia/ammonium and/or free calcite. By-products are excess material to be reduced through optimization and/or accounted for in influent formulations. Ammonia as a recoverable byproduct has commercial value in both fertilizer and alternative fuel applications.

There are at least two ammonia extraction methods. First, granular zeolite cliniptilolite mineral aggregate is used as an air filter for extracting ammonia gas, and as a liquid filter for extracting ammonium from effluent. Ammonia-saturated zeolite has potential applications as a fertilizer, fertilizer additive, and/or fertilizer component. Second, an electrode based system is used for conversion of aqueous ammonia/ammonium as a hydrogen fuel source for electricity production.

Effluent, further treated or not, is a fuel source for other ammonia-based energy production technologies and recycling technologies including recycling of water, calcite and by-products.

Settling tanks, mesh filters, fabrics and/or hydrocyclones are used for the removal of free calcite in solution wherein, and preferably, the micro-organisms remain. This material is an inoculation source for new biocement formation and fertilizer applications (calcium available for plant cell wall formation, and microbes available for soil denitrification).

Example 3

Biologically-formed Microcrystalline Calcium Carbonate was produced using a urease-producing microorganism (*S. pasteurii*) grown in a liquid fermentation medium containing urea. The media was agitated to create a uniform suspension. At late stage growth of the culture, calcium ions were added in the form of a calcium chloride solution to a saturation of molar equivalency with the urea. Urease activity results in the hydrolysis of urea ($2NH_2CO$) into ammonium ($NH_4$) and carbon (C). Carbon combines with calcium (Ca) to produce calcium carbonate ($CaCO_3$). Calcium carbonate crystals formed ranged in size from 50 µm to 0.1 µm and generally "regular" (e.g., spherical) in shape. Calcium carbonate was separated from the solution using one or more of centrifugation, settling tanks, hydro-cyclones, or decanting. The method was performed as a batch process and also as a continuous production line.

A variation of this method was used to increase particle size by using fine aggregate materials to create an agglomerate, which also improved liquid-solid separation. In this variation, fine aggregate with a Mesh Scale of 70 micron size was added to the solution during the fermentation process and at a quantity that did not exceed the ability for the agitation to keep the fine aggregates in suspension. Following the addition of calcium ions, the calcite bonds to, and bonds together the fine aggregate, creating larger, heavier particles.

Example 4

The method of Example 3 is performed with co-culture of a second organism, *Delaya venusta*. The co-culture process is developed for a single fermentation within a single reactor, alternating fermentations within a single reactor, or by circulating media between two separated fermentations in separate reactors, wherein the reactor is either a liquid state reactor (e.g., batch, batch-fed, or continuous), or a solid-state reactor such as an aggregate-unit (e.g., bricks).

Example 5

In another example, a first composition is prepared containing an aqueous mixture of viable cells or spores of urease-producing microorganisms suspended within a transport media that promotes viability and not growth and/or germination of spores, but with minimal or no calcium. A second composition is prepared that contains an aqueous form of calcium, calcium chloride. A third composition is prepared containing urea and ingredients for growth of the microorganisms or, alternatively, the urea is added to the first composition and the ingredients are added to the second composition. The compositions are than applied to an area simultaneously or sequentially and, if sequentially, in any order. To an area such as a mining operation, dust in the atmosphere is significantly reduced and mostly eliminated.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of dust control, comprising:
   determining a temperature of use;
   selecting an amount of nitrogen and calcium sources and an amount of enzyme to solidify a slurry within a particular time frame based on the temperature of use, the nitrogen source comprises urea;
   creating a composition that includes the amount of nitrogen and calcium sources and spores for producing the amount of enzyme, the spores comprise spores of a urease-producing microorganism;
   distributing the composition over a surface, the distributing the composition includes distributing the nitrogen and calcium sources in a timed-release form with a pre-determined rate of dissolution;
   germinating the spores on the surface to produce calcite to form a self-renewable crust at the surface; and
   generating the slurry to recreate the self-renewable crust at the surface by applying water to the surface without the reapplication of the composition to the surface.

2. The method of claim 1, wherein the composition includes nutrients that promote the proliferation of the spores.

3. The method of claim 2, wherein the distributing the composition includes distributing the nutrients in a timed-release form with a particular rate of dissolution.

4. The method of claim 1, wherein the composition includes a transport medium which maintains viability of the spores without propagation and support material that is inorganic and porous.

5. The method of claim 1, wherein the composition includes aggregate of only 0.5 mm or less in diameter.

6. The method of claim 1, wherein the surface is more resistant to erosion after applying the composition.

7. The method of claim 1, wherein the surface is a walking path, a pile, a cliff or vehicle roadway.

8. The method of claim 1, wherein the composition is a liquid, a gel, a slurry, a sludge, a semisolid, or dry powder.

9. The method of claim 1, wherein the spores are spores of *Sporosarcina pasteurii, Sporosarcina ureae, Proteus vulgaris, Bacillus sphaericus, Myxococcus xanthus, Proteus mirabilis, Helicobacter pylori*, or variants, serotypes, mutations or combinations thereof.

10. The method of claim 2, wherein the nutrients comprise one or more of water, vitamins, minerals, amino acids, proteins, oils, fatty acids, saccharides and polysaccharides.

11. The method of claim 1, wherein the distributing comprises spraying, coating, misting, or painting the composition onto the surface or immersing the surface into the composition.

12. The method of claim 1, wherein the calcium source comprises calcium chloride, calcium acetate, calcium phosphate, calcium carbonate, calcium lactate, or calcium nitrate.

13. The method of claim 2, wherein the spores are encapsulated or coated with the nutrients.

14. The method of claim 1, wherein the surface comprises sand, gravel, rock, dirt, glass, wood, paper, metal, plastic, polymers, fibers, minerals or combinations thereof.

15. The method of claim 1, wherein the surface is a natural geological or man-made surface comprising a cliff, a dune, an aggregate pile, a ledge, a supporting wall, a foundation, tailings, piles of waste materials from a manufacturing process, or a structure for which support or reinforcement is desired.

16. The method of claim 1, wherein the composition comprises a coloring agent, an identifying agent or a detectable marker.

17. The method of claim 1, wherein the distributing the composition to the surface reduces dust and other particulate materials generated from the surface as compared to an unapplied surface.

18. The method of claim 17, wherein the dust and other particulate materials generated from the surface comprise sand, glass, wood, pulp, sawdust, lignin, metal, polymers, fines, micro-cellulose, waste materials, ash, scrubber waste, biomass, moss, hay, straw, grass, sticks, leaves, algae, dirt, ash, particulate material, refuse, spores, carbon, soot, materials from cement, block, or brick manufacturing, materials from foundry operations, materials from grinding limestone, materials from sand tailings, materials from mining, materials from smelters, materials from paint manufacturing, byproducts from manufacturing operations, or combinations thereof.

19. The method of claim 17, wherein calcium carbonate formed at the surface covers or encapsulates the dust.

20. The method of claim 1, wherein the applying the composition reduces or eliminates dust.

* * * * *